United States Patent [19]
Fogg et al.

[11] Patent Number: 6,045,589
[45] Date of Patent: Apr. 4, 2000

[54] METHODS OF COLORING HAIR OR EYELASHES WITH COMPOSITIONS WHICH CONTAIN METAL CONTAINING PIGMENTS AND A COPAIBA RESIN

[75] Inventors: Stanley Ray Fogg, Shoreview; Timothy Roland Kapsner, Minneapolis; Peter Matravers, Plymouth, all of Minn.

[73] Assignee: Aveda Corporation, Minneapolis, Minn.

[21] Appl. No.: 09/241,019

[22] Filed: Feb. 1, 1999

Related U.S. Application Data

[62] Division of application No. 09/067,632, Apr. 28, 1998, Pat. No. 5,888,251.

[51] Int. Cl.⁷ ....................................................... A61K 7/06
[52] U.S. Cl. .............................. 8/405; 8/637.1; 424/70.6; 424/70.7; 424/70.11; 424/74
[58] Field of Search ................. 8/405, 550, 552, 8/580, 623, 626, 637.1, 931, 404; 424/70.6, 70.7, 70.11, 74; 132/203, 208, 209

[56] References Cited

U.S. PATENT DOCUMENTS

| | | | |
|---|---|---|---|
| 3,756,165 | 9/1973 | Valiela | 101/483 |
| 3,926,659 | 12/1975 | Bernhard et al. | 106/418 |
| 3,951,679 | 4/1976 | Bernhard et al. | 106/418 |
| 4,938,954 | 7/1990 | Gross et al. | 8/405 |
| 5,679,114 | 10/1997 | Haning et al. | 8/405 |
| 5,830,446 | 11/1998 | Berthiaume et al. | 424/70.1 |

FOREIGN PATENT DOCUMENTS

| | | |
|---|---|---|
| 93-02003 | 9/1993 | Brazil . |
| 9301950 | 9/1993 | Brazil . |
| 9302003 | 9/1993 | Brazil . |
| 463780 | 1/1992 | European Pat. Off. . |
| WO 98/05294 | 2/1998 | European Pat. Off. . |
| 2692480 | 12/1993 | France . |
| 5-043431 | 2/1993 | Japan . |
| 2149806 | 6/1985 | United Kingdom . |
| 98/05294 | 2/1998 | WIPO . |

OTHER PUBLICATIONS

Forster, Corporate Report–Minnesota, published Jun. 1998—(Abstract).

Del Nunzio et al., Aerosol Cosmet., 7(41): 7–9, 1985—(Abstract) (No Month Available).

"Anita Roddick in Search of Folk Cosmetics", Cosmetics and Toiletries Manufacturers & Suppliers, Cosmetics & Toiletries Manufacturers & Suppliers, Sep. 1991, pp. 16.

CAPLus Abstract of Del Nunzio, "Copaiba Oil Use In Cosmetics," Aerosol Cosmetics (1985) (no month available).

*Primary Examiner*—Caroline D. Liott
*Attorney, Agent, or Firm*—Karen A. Lowney, Esq.

[57] ABSTRACT

A hair treatment composition for coloring the hair upon the scalp and an eyelash mascara is disclosed. The hair is typically colored with a mascara brush to achieve streaking and a non-homogenous coloring of the hair upon the scalp or the eyelash. A copaiba resin and a metal containing pigment are combined to obtain the hair coloring product. The resultant product is applied to the hair upon the scalp or the eyelash to effect coloring of the hair upon the scalp or the eyelash.

19 Claims, No Drawings ably iron oxide powder, and a silicone oil. The Nakumura United Kingdom patent optionally includes a propellant.

METHODS OF COLORING HAIR OR EYELASHES WITH COMPOSITIONS WHICH CONTAIN METAL CONTAINING PIGMENTS AND A COPAIBA RESIN

This application is a division of U.S. application Ser. No. 09/067,632 filed Apr. 28, 1998, now U.S. Pat. No. 5,888,251.

BACKGROUND OF THE INVENTION

1. Field of the Invention

The present invention deals with hair care products. In particular, the present invention deals with hair care products employed to color the hair upon the scalp with streaks (non-homogenous manner), and particularly products to temporarily color the hair upon the scalp.

2. Description of the Art Practices

Various products are known for use in permanently coloring the hair. A major problem in coloring of the hair is that the user of the product often does not care for the color after it has been applied. The use of permanent hair colors may also prevent the user from wearing certain items of the wardrobe which conflict with the newly selected and applied hair color. When the prospective user of the hair color merely wants to determine how the hair color will appear, the use of a permanent product is not desirable.

The reader is directed to the following references for the general discussion of hair care products. U.S. Pat. No. 4,992,077 issued Feb. 12, 1991 to Tennigkeit, et. al., discusses the use of oxidative dyes in a creme or gel form. Tennigkeit, in U.S. Pat. No. 5,006,127, issued Apr. 9, 1991 further discusses oxidative dyes in creme or gel form.

Bartuska, in U.S. Pat. No. 4,183,366 issued Jan. 15, 1980, discusses henna-based hair coloring and/or hair conditioning compositions. The compositions of Bartuska are stated to contain non-ionic surface active agents, water soluble polymers, and quaternary salts.

Andrean, in U.S. Pat. No. 5,205,837, issued Apr. 27, 1993, describes powder form products containing at least one synthetic melanotic pigment formed in situ by oxidation of an indole compound. The Andrean products are stated to be for use in dyeing hair.

Gross, et. al., in U.S. Pat. No. 4,938,954, issued Jul. 3, 1990, describes hair wax compositions containing polyethylene glycol, a hydrogenated castor oil which is ethoxylated, glycerol or ethyl hexane diol, and/or a lower molecular weight polyethylene glycol, and water.

Hahn, in U.S. Pat. No. 4,873,079, issued Oct. 10, 1989, describes temporary or semipermanent hair coloring compositions. The compositions of Hahn are stated to comprise an aqueous vehicle having a hair coloring component. The compositions of Hahn are stated to further include a co-solvent for the hair colorant which is a diol selected from a group consisting of aliphatic hydrocarbon diols having from 5 to 8 carbon atoms and bis-(hydroxy-alkyl) cyclohexanes having from 7 to 14 carbon atoms. Hair care products are also disclosed in Haning et al., 5,679,114, issued Oct. 21, 1997.

United Kingdom patent application 2 149 806 A to Nakumura, which published Jun. 19, 1985 describes in hair coloring compositions comprising colored mica, and optionally iron oxide powder, and a silicone oil. The Nakumura United Kingdom patent optionally includes a propellant.

The present invention employs naturally occurring oleoresins commonly referred to as copaiba resin. Copaiba resins have been disclosed for use as beverage clouding agents in U.S. Pat. 3,959,510 issued May 25, 1976 to Felton et al.

Copaiba resins have also been described as having useful properties in a process of producing electrophotographic copying material in U.S. Pat. No. 3,640,709 issued Mar. 14, 1972 to Tabuko et al. U.S. Pat. No. 3,649,263 issued to Kondo et al., Mar. 14, 1972 further describes binders for electro-photographic compositions containing naturally occurring resins The present invention deals with hair color products to achieve streaking of the hair upon the scalp or for eyelash mascara products. The hair color products of the present invention are utilized to achieve streaking of the hair upon the scalp or to color the eyelash. The hair color products of the invention for use upon the scalp are temporary in nature. By temporary it is meant that the color added to the hair will wash out upon shampooing the hair. By being of a temporary nature the color of the hair upon the scalp may be changed one or more times per day by washing of the hair upon the scalp.

The mascara products are formulated to be retained upon the eyelash through one or more cleansings. One or more water insoluble waxes are added to a mascara product to ensure that the mascara remains upon the eyelashes. In either the product intended for the hair upon the scalp or the eyelash mascara it has been found that the compositions of the present invention are substantially non-migrating and substantially do not rub off. The foregoing is important to prevent the composition form being transferred to articles of clothing and to avoid eyelashes sticking together.

To the extent that the foregoing references are applicable to the present invention they are herein specifically incorporated by reference. Throughout the specification and claims, percentages and ratios are by weight unless otherwise indicated. Parts are determined on the basis of 100 parts of the end use composition. Ranges and ratios may be combined. Temperatures given herein are degrees Celsius unless otherwise indicated.

SUMMARY OF THE INVENTION

The present invention describes a hair treatment composition comprising:
 a. a copaiba resin; and,
 b. a metal containing pigment.

The present invention also describes a hair treatment composition comprising:
 a. *Maracaibo copaiba* resin;
 b. a metal oxide coated mica where the metal source is a member selected from the group consisting of iron and titanium provided further that the metal oxide coated mica has a mean particle size distribution of about 5 to about 100 microns;
 c. an emulsifier; and,
 d. water.

The present invention also describes a method of treating hair upon the scalp to temporarily color the hair upon the scalp including the steps of contacting the hair upon the scalp with a composition:
 a. copaiba resin;
 b. a metal containing pigment, and;
 c. water; for a time sufficient to impart a color to the hair upon the scalp.

The present invention further describes a method of treating the eyelash to color the eyelash including the steps of contacting the eyelash with a composition comprising:

a. copaiba resin;
b. a metal containing pigment, and;
c. water; for a time sufficient to impart a color to the eyelash.

DETAILED DESCRIPTION OF THE INVENTION

The Resin Component

The first component to be discussed in the present invention is a copaiba resin component. The copaiba resin component is particularly important to the present invention in that it allows suspension of the metal containing metal containing pigment in the composition of the invention.

The copaiba resin is included in the composition of he present invention to ensure the stickiness of the composition allowing dye and layers to be built up and attach to the hair upon the scalp. The copaiba resin has been found in the compositions of the present invention substantially prevent migration of the pigment and to substantially avoid the rub off the product upon clothing.

Historically, resins used in hair treatment products the last 100 years have contained synthetic resins. The copaiba resin utilized in the present invention is obtained from natural sources and is a renewable resource. The copaiba resin is derived from the Copaiba tree found in Brazil. Collection of the resin is by environmentally friendly methods.

Copaiba is an oleo-resin obtained from the trunk of *Copaifera lansdorfi* Desfontaines, family Leguminoseae, and other species of Copaifero. The trees from which the copaiba resin is obtained are large trees indigenous to Brazil and the North of South America.

The copaiba resin, an oleo-resin, is contained in secretion ducts that form an extensive network in each zone of the secondary wood of both stem and root the Copaiba tree, extending throughout the entire length of the zone. These ducts are formed in the young wood and rapidly attain their normal diameter, which is often very considerable; at the level of the insertion of the branches number of lateral ducts connect zone with zone. The oleo-resin is collected by cutting in the trunk of the trees near the base a cavity sloping inwards and downwards, and penetrating to the center of the trunk, resembling the "box" made in the trunk of the turpentine trees.

Into the cavity the copaiba resin is discharged; it is then transferred to barrels and other vessels for exportation. As much as 48 liters have been obtained from a single tree.

The resin is imported from Para, Maranham, Maracaibo, Bahia, Cartagena, these resins giving their names to the commercial varieties, which differ in the percentage of volatile oil and of resin, and in the composition of the latter.

The resin as well as being of high performance in the product contains an intrinsic essential oil (pure essence) which makes the resin sweet smelling unlike the synthetic resins whose fragrance is not very pleasant. The chemical composition of the copaiba resin is a complex mixtures of different chemical types of substances. These substances include acids, esters, and glycosides.

*Maracaibo copaiba* is the preferred copaiba resin for use in the present invention. The *Maracaibo copaiba* resin is a clear, viscous, brown-yellowish fluid with a slight but distinct green fluorescence.

The *Maracaibo copaiba* resin possesses a characteristic aromatic odor and an unpleasant, acrid and rather bitter taste. The specific gravity (density) of the copaiba resin at 20° C. is about 0.950 g/ml to about 0.999, preferably about 0.958 g/ml to 0.993 g/ml. The usefulness of the resin, in part is because it is very close to the density of water in which the resin is dispersed and thereby forms stable emulsions. The proportion of volatile oil in the *Maracaibo copaiba* resin varies from about 35 to 50 per cent.

The following is a description of *Maracaibo copaiba* resin properties from *Copaifera lansdorfi* Desfontaines:

A more or less viscous, yellow to golden-brown liquid, generally transparent and sometimes fluorescent; odor characteristic and persistent; taste slightly bitter, acrid and persistent.

Miscible with dehydrated alcohol, ether, carbon disulphide, fixed and volatile oils; soluble in an equal volume of light petroleum (boiling-point 50 to 60 C.), the addition of a further quantity of the solvent producing a flocculent precipitate; 3 ml added to 1 ml of dilute ammonia solution gives a clear solution.

Acid value of 120 to 160, calculated with reference to the residue obtained by drying on a water-bath.

Non-volatile matter when heated on a water-bath until all the volatile oil has been driven off is 50 to 65 percent residue.

Optical rotation of the volatile oil obtained by distillation with steam or under reduced pressure, −7 to −35.

Common adulterant testing. Turpentine and other foreign matter. When heated on a water-bath, no odor of turpentine is observed, and, after all the volatile oil has been driven off, a resin remains which, when cold, is hard and brittle.

The Metal Pigment

The metal containing pigment of the present invention is typically the component which provides the color to the hair upon the scalp. The metal containing pigment typically contains titanium dioxide or iron oxide. The metal containing pigment is preferably deposited (coated) on mica for the hair upon the scalp compositions. The mica adds a glitter effect to the hair upon the scalp compositions. The mica is typically omitted from a product intended for use upon the eyelashes.

Suitable titanium dioxide and iron oxide treated mica pigment products for use in the present invention may be obtained from the Engelhard Corporation, Pigments & Additives Group, 101 Wood Avenue Iselin, N.J. 08530-0770. Preferred pigments are those obtained from Engelhard as Cloisonne Super Gold™ product number 232Z. A further preferred pigment is Cloisonne Superbronze™ product number 250Z.

Further suitable titanium dioxide and iron oxide treated mica products are obtainable from the EM Pigment Division of Rona. Rona is located at 5 Skyline Drive Hawthorne, N.Y. A preferred Rona product is Colorona Bordeaux™, pigment.

The particle size range for the metal oxide coated mica component is conveniently from about 5 microns to about 150 microns. Preferably, the mean particle size distribution of the metal oxide coated mica component is from about 25 to about 50 microns. The composition of a typical iron oxide coated mica is about 55 to 59% mica and about 41 to 45% iron oxide. The product has a bulk density as measured by a Scott Volumeter of 2.5 to 3.0 grams per cubic inch. The pH of a 10% aqueous suspension of the iron oxide coated mica is from 3 to 6. The product is observed to absorb linseed oil at about 75 g per 100 g of pigment.

A typical mica and titanium dioxide/iron oxide product is from 51 to 61% mica, 34 to 40% titanium dioxide, and 5 to 9% iron oxide. The bulk density of the above product is from 3.0 to 3.5 grams per cubic inch. The pH of a 10% aqueous suspension of the pigment is about 8. The pH of the final composition of the invention and the in use pH of the product are both about 7 to about 8, preferably about 7.1 to about 7.8.

Product Preparation

The product of the invention is prepared by combining the various ingredients in a suitable mixing vat. Water is added to the vat and stirring is initiated. The ingredients are generally added in the order of the water, the metal containing pigment, and then the copaiba resin. While the ingredients, including any optional ingredients, may be added in any order it is preferred that the above order of mixing the ingredients be followed.

Any remaining ingredients, including preservatives, fragrances and anti microbial materials may be added at any point in the process where the added ingredient maintains its intended function and where the added ingredient does not interfere with the remainder of the product.

Product Utilization

The product of the invention is applied to the hair upon the scalp, preferably following a thorough cleansing of the hair upon the scalp. The product of the invention is applied with a mascara type brush although it may be applied with the fingers or with a cloth or toilet tissue. For the best results in applying the product of the invention to the hair upon the scalp it is suggested that the hair upon the scalp be wet when the product is applied.

Suitable surfactants (detergents) for cleaning the hair upon the scalp prior to applying the composition of the present invention are described below. The same surfactant materials will remove the hair upon the scalp coloring thus rendering the use of the product temporary.

Suitable anionic surfactants are those generally incorporated into a shampoo product. Generally, the anionic surfactant is a water-soluble alkyl or alkyl aryl sulfonate having from about 8 to about 22 carbons, preferably from about 12 to about 18 carbons, in the alkyl radical, which may be straight or branched chain, and also includes such classes of compounds ethoxylated with from 1 to 5 mols, preferably 1 to 3 mols, ethylene oxide per molecule. The sulfate or sulfonate group is typically base-neutralized to provide an alkali metal, especially sodium or potassium, ammonium, or mono, di-, or trialkanolium cation.

Illustrative anionic surfactants of the above-named classes include: Sodium cetyl sulfate, sodium myristyl sulfate, sodium lauryl sulfate, sodium tallow sulfate, sodium decyl sulfate, sodium decylbenzene sulfonate, sodium tridecylbenzene sulfonate, sodium C 14 to C 16 olefin sulfonate, sodium C 12 to C 15 alcohol sulfate, sodium lauryl ether sulfate, sodium myristyl ether sulfate, sodium polyoxyethylene (5 mols ethylene oxide) lauryl ether sulfate, sodium polyoxyethylene (12 mols ethylene oxide) lauryl ether sulfate, sodium nonylphenyl ether sulfate, sodium polyoxyethylene (1 to 4 mols ethylene oxide), C 12 to C 15 alkyl ether sulfate, sodium lauryl sulfoacetate.

Synthetic anionic detergents useful herein include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight C 12-13 compounds; from 60 to 100% by weight of C 14-15-16 compounds, from about 0 to 20% by weight of C 17-18-19 compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Other suitable anionic detergents utilizable herein are olefin sulfonates having about 12 to about 24 carbon atoms. The term "olefin sulfonates" is used herein to mean compounds which can be produced by the sulfonation of an alpha-olefin by means of uncomplexed sulfur trioxide, followed by neutralization of the acid reaction mixture in conditions such that any sultones which have been formed in the reaction are hydrolyzed to give the corresponding hydroxy-alkane sulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $So_2$, etc., when used in the gaseous form.

The alpha-olefin from which the olefin sulfonates are derived are mono-olefin having 12 to 24 carbon atoms, preferably 14 to 16 carbon atoms. Preferably, they are straight chain olefin. Examples of suitable 1-olefin include 1-dodecene; 1-tetradecene; 1-hexadecene; 1-octadecene; 1-cicosene and 1-tetraeosene.

Additional surfactant materials which may be utilized herein include the following exemplified materials. Long Chain tertiary amine oxides corresponding to the following general formula:

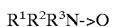

wherein $R^1$ contains an alkyl, alkenyl or monohydroxy alkyl radical of from about 8 to about 18 carbon atoms, from 0 to about 10 ethylene oxide moieties, and from 0 to 1 glyceryl moiety, and $R^2$ and $R^3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semi-polar bond between the nitrogen and the oxygen.

Examples of amine oxides suitable for use in this invention include dimethyldodecyl-amine oxide, oleyldi(2-hydroxyethyl)amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, and dimethyl-hexadecylamine oxide.

Further additional surfactants include long chain tertiary phosphine oxides corresponding to the following general formula:

RR'R"P->O wherein R contains an alkyl, alkenyl or monohydroxyalkyl radical ranging from 8 to 18 carbon atoms in chain length, from 0 to about 10 ethylene oxide moieties and from 0 to 1 glyceryl moiety and r' and r" are each alkyl or monohydroxyalkyl groups containing from 1 to 3 carbon atoms. The arrow in the formula is a conventional representation of a semi-polar bond between the phosphorus and the oxygen.

The hair coloring formulation is added to the hair upon the scalp, and thoroughly worked into the hair upon the scalp by the consumer. The level of application of the product is such that the copaiba resin, to the weight of the dry hair upon the scalp treated is about 0.01 to 0.5 grams per gram of hair upon the scalp. Unlike other coloring formulations it is not necessary to rinse the consumer's hair upon the scalp after applying the product.

The product is conveniently applied to the hair upon the scalp at room temperature to slightly elevated temperatures, e.g. 18 to 38 degrees Celsius. As the product has a viscosity of about 130,000 c. p. s., it will be applied as a thick liquid. Thus, the product, is not particularly prone to spillage if dropped by the consumer.

If desired, the new color tint of the hair upon the scalp may be retained by first applying the hair coloring composition of the invention and thereafter applying a fixative hair spray. Suitable fixative hair upon the scalp sprays include PVM MA (polyvinyl methacrylate maleic anhydride copolymer) in SD 40 alcohol. The color will be retained longer by the use of a fixative hair spray as the color is then more resistant to brushing out of the hair color.

Amounts of the Components

The copaiba resin is typically utilized at about 0.25 to about 15 percent by weight of the composition, preferably at about 2 to about 20 percent by weight of the composition, more preferably about 4 to about 17 percent by weight of the composition, and most preferably about 5 to about 14 percent by weight of the composition.

The metal containing pigment of the present invention is typically utilized at about 0.5 to about 40 percent by weight of the composition, preferably at about 4 to about 40 percent by weight of the composition, more preferably about 6 to about 30 percent by weight of the composition, and most preferably about 8 to about 22 percent by weight of the composition. When using a metal oxide coated mica, it is preferably present in an amount of about 0.5 to about 10 percent by weight of the composition.

The water in the present invention is typically utilized at about 40 to about 90 percent by weight of the composition, more preferably about 55 to about 85 percent by weight of the composition, and most preferably about 60 to about 80 percent by weight of the composition.

Optional Ingredients

The products described herein can contain a variety of nonessential optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea.

Further optional ingredients include conditioning agents such as cationic surfactants. Examples of cationic surfactants include tricetyl methyl ammonium chloride, cetyl trimethyl ammonium chloride, stearyldimethyl benzyl ammonium chloride, and di-(partially hydrogenated tallow) dimethylammonium chloride.

The hair coloring compositions of the present invention to the hair are compatible with and may include a hair conditioning agent. Additional ingredients include thickeners and viscosity modifiers such as a diethanolamide of a long chain fatty acid (e.g., PEG 3 lauramide) cocomonoethanolamide, amine oxides, block polymers of ethylene oxide and propylene oxide such as Pluronic F88 offered by BASF Corpoorationin Wyandotte, Mich.; fatty alcohols such as cetearyl alcohol, sodium chloride, sodium sulfate, magnesium aluminum silicate, cellulose gum (and other gums such as tamarind, guar or hydroxypropyl cellulose), polyvinyl alcohol, and ethyl alcohol; pH adjusting agents such as citric acid, sodium citrate, succinic acid, phosphoric acid, sodium hydroxide, potassium hydroxide, sodium carbonate, etc., perfumes; dyes; and, sequestering agents such as disodium ethylenediamine tetraacetate. Such agents generally are used individually at a level of from about 0.01% to about 10%, preferably from about 0.5% to about 5.0% by weight of the composition.

Additional optional ingredients in the present invention include emulsifiers at about 0.05 to 10 percent by weight of the composition. The emulsifier is conveniently utilized at about 0.10 to 5 percent by weight, and most preferably 0.20 to 3 percent by weight of the composition An emulsifier is included to aid in forming a homogenous product in the form of an oil-in-water emulsion. The composition may also optionally contain an emollient.

Further ingredients which may be added are free saturated fatty acids such as lauric, myristic, palmitic and stearic acids. A useful unsaturated fatty acid is oleic acid. The fatty acids aid in emulsifying the product of the invention. Waxes such as Carnuba and beeswax are often added to the mascara product of the invention. The wax adds water insoluble properties to the composition and thereby adds permanence to the eyelash mascara.

What follows is an example of the preparation of the composition of the present invention:

EXAMPLE I

A hair coloring composition of the present invention is prepared by adding 69.1 parts of deionized water, based upon the total composition weight, to a mixing vat. To the deionized water is added 1.5 parts of magnesium aluminum silicate based upon the total composition weight to form a first mixture. Mixing is initiated and the mixture of the deionized water and the magnesium aluminum silicate is heated to about 75° C. to 80° C.

A second mixture is formed comprising 0.15 part potassium hydroxide based upon the total composition weight, mica at 8.0 parts based upon the total composition weight, and iron oxide at 10.0 parts based upon the total composition weight. The second mixture is then added with mixing to the first mixture. The temperature of the resultant third mixture is maintained at about 75° C. to 80° C.

A fourth mixture is formed by adding 6.0 parts of copaiba resin based upon the total composition weight, glyceryl stearate at 0.5 parts based upon the total composition weight, and stearic acid at 2.0 parts based upon the total composition weight. The fourth mixture is then added with stirring to the third mixture to form a resultant fifth mixture. The temperature of the resultant fifth mixture is maintained at about 75° C. to 80° C.

A sixth mixture is formed comprising 1.0 part phenoxyethanol based upon the total composition weight, methylparaben at 0.30 part based upon the total composition weight, and propylparaben at 0.20 part based upon the total composition weight. The sixth mixture is then added with stirring to the fifth mixture. The temperature of the resultant seventh mixture is maintained at about 75° C. to 80° C. for one-half hour to ensure thorough mixing.

The resultant seventh mixture is thereafter cooled to about 20° C. The resultant seventh mixture is then obtained as an oil-in-water emulsion having a pH of about 7.5. The product is then applied to the hair as described above.

The products of the present invention have the advantage of temporarily changing the hair color without chemically damaging the hair upon the scalp in the manner in which bleaching changes the hair.

As the product is temporary in nature it may be utilized for selectively treating portions of the hair upon the scalp such as bangs or the temples with out the risk of over doing the treatment area on a permanent basis.

EXAMPLE II

An eyelash mascara composition of the present invention is prepared by adding 50.8 parts of deionized water, based upon the total composition weight, to a mixing vat. To the deionized water is added 1.5 parts of magnesium aluminum silicate and 10.0 parts arabinogalactin resin based upon the total composition weight to form a first mixture. Mixing is initiated and the mixture of the deionized water and the magnesium aluminum silicate is heated to about 75° C. to 80° C.

A second mixture is formed comprising 0.2 parts hydroxyethyl cellulose and 2.0 parts glycerin both based upon the total composition weight.

A third mixture is formed comprising 1.0 part ammonium hydroxide based upon the total composition weight, silica at 3.0 parts based upon the total composition weight, and iron oxide at 12.0 parts based upon the total composition weight. The second and third mixtures are then added with mixing to the first mixture. The temperature of the resultant fourth mixture is maintained at about 75° C. to 80° C.

A fifth mixture is formed by adding 3.0 parts of copaiba resin based upon the total composition weight, carnuba wax at 3.0 parts based upon the total composition weight, glyceryl stearate at 4.0 parts based upon the total composition weight, beeswax at 6.0 parts based upon the total composition weight, and stearic acid at 2.0 parts based upon the total composition weight. The fifth mixture is then added with stirring to the fourth mixture to form a resultant sixth mixture. The temperature of the resultant sixth mixture is maintained at about 75° C. to 80° C.

A seventh mixture is formed comprising 1.0 part phenoxyethanol based upon the total composition weight, methylparaben at 0.30 part based upon the total composition weight, and propylparaben at 0.20 part based upon the total composition weight. The seventh mixture is then added with stirring to the sixth mixture. The temperature of the resultant eighth mixture is maintained at about 75° C. to 80° C. for one-half hour to ensure thorough mixing.

The resultant eighth mixture is thereafter cooled to about 25° C. The resultant eighth mixture is then obtained as an oil-in-water emulsion having a pH of about 7.5. The product is then applied to the eyelashes as described above.

Having described the invention, the following is claimed:

1. A hair treatment composition comprising:

a. a *Maracaibo copaiba* resin;

b. a metal containing pigment, c. an emulsifier; and, d. water.

2. The composition of claim 1 wherein the density of the copaiba resin at 20° C. is about 0.950 g/ml to to about 0.999 g/ml.

3. The composition of claim 1 wherein the metal containing pigment has a mean particle size distribution of about 5 to about 100 microns.

4. The composition of claim 1 wherein the metal containing pigment is a metal oxide coated mica.

5. The composition of claim 1 wherein the copaiba resin has a density at 20° C. is about 0.958 g/ml to 0.993 g/ml.

6. The composition of claim 1 wherein the metal containing pigment has a mean particle size distribution of about 25 to about 50 microns.

7. The composition of claim 1 which is an oil-in-water emulsion.

8. The composition of claim 1 wherein the copaiba resin is present at about 0.25 to about 15 percent by weight of the composition.

9. The composition of claim 4 wherein the metal oxide coated mica has as the metal source a member selected from the group consisting of iron and titanium, and mixtures thereof.

10. The composition of claim 1 further containing an emollient.

11. The composition of claim 1 wherein the pH is about 7 to about 8.

12. The composition of claim 1 further containing at least one wax.

13. A hair treatment composition comprising:

a. *Maracaibo copaiba* resin;

b. a metal oxide coated mica where the metal source is a member selected from the group consisting of iron and titanium provided further that the metal oxide coated mica has a mean particle size distribution of about 5 to about 100 microns;

c. an emulsifier, and;

d. water.

14. The composition of claim 13 wherein the metal oxide coated mica is present at about 0.5 to 10 percent by weight of the composition.

15. The composition of claim 13 wherein the composition is an oil-in-water emulsion.

16. The composition of claim 13 wherein the pH is about 7 to about 8.

17. The composition of claim 13 wherein the emulsifier is at about 0.1 to 5 percent by weight of the composition.

18. The composition of claim 13 wherein the water is present at about 40 to about 90 percent by weight of the composition.

19. The composition of claim 1 wherein the metal containing pigment is a metal oxide selected from the group consisting of titanium dioxide, iron oxide, and mixtures thereof.

* * * * *